United States Patent [19]

Norton

[11] Patent Number: 4,782,016

[45] Date of Patent: * Nov. 1, 1988

[54] ANALYTICAL ELEMENT AND METHOD FOR DETERMINATION OF THEOPHYLLINE BY ENZYME INHIBITION

[75] Inventor: Gary E. Norton, Rochester, N.Y.

[73] Assignee: Eastman Kodak Company, Rochester, N.Y.

[ * ] Notice: The portion of the term of this patent subsequent to Nov. 1, 2005 has been disclaimed.

[21] Appl. No.: 692,473

[22] Filed: Jan. 18, 1985

[51] Int. Cl.$^4$ .................. C12Q 1/42; C12N 9/99
[52] U.S. Cl. ................................ 435/21; 435/7; 435/184; 435/805; 436/822
[58] Field of Search ............ 435/21, 184, 805, 810, 435/7; 422/56; 436/825, 822

[56] References Cited

U.S. PATENT DOCUMENTS

| | | | |
|---|---|---|---|
| 4,042,335 | 8/1977 | Clément | 435/805 X |
| 4,264,727 | 4/1981 | Kolehmainen et al. | 435/8 |
| 4,555,484 | 11/1985 | La Rossa et al. | 435/21 |

OTHER PUBLICATIONS

Good et al, Biochem., 5(2); 467–477 (1966).
Harada et al., Arch. Oral Biol., 27(1):69–74 (1982).
Williams et al., J. Chem. Soc., Perkins Trans., 2(1):25–33 (1973).
Vinet et al, Clin. Chem., 25:8, pp. 1370–1372 (1979).
Vinet et al, Clin. Biochem., 11:2, pp. 57–61 (1978).
Fawaz et al, Z. Physiol. Chem., 353, pp. 1779–1783 (1972).
Ansari et al, Clinica Chimica Acta, 118, pp. 135–139 (1982).

*Primary Examiner*—Esther M. Kepplinger
*Attorney, Agent, or Firm*—J. Lanny Tucker

[57] ABSTRACT

Theophylline can be determined with an analytical element, composition, kit and method which utilize the inhibition, by theophylline, of alkaline phosphatase activity on an appropriate substrate. The assay is carried out at a pH of 9 or less. The element comprises an absorbent carrier material, a suitable buffer for maintaining the pH at 9 or less, and, in fluid contact, a first zone containing an isoenzyme of alkaline phosphatase which is capable of activity at pH 9 or less, and a second zone containing a substrate for the isoenzyme. Use of this invention avoids the effect of endogenous alkaline phosphatase found in human biological fluids which has no activity at pH 9 or less.

15 Claims, No Drawings

ANALYTICAL ELEMENT AND METHOD FOR DETERMINATION OF THEOPHYLLINE BY ENZYME INHIBITION

FIELD OF THE INVENTION

The present invention relates to clinical chemistry and to the assay of human biological fluids for theophylline. More specifically, it relates to a dry analytical element, analytical composition, diagnostic kit and a method for the determination of theophylline in human biological fluids.

BACKGROUND OF THE INVENTION

Theophylline is a drug frequently administered for treatment of asthma and pulmonary diseases. For the drug to be used successfully without serious side-effects, it must be frequently and carefully monitored in a patient because it has a relatively narrow therapeutic range of use, i.e. 1-2 mg/dl.

Numerous techniques have been used to determine the amount of theophylline in human serum. Most of these techniques have serious drawbacks. For example, known spectrophotometric methods require large sample volumes, extensive pretreatment and suffer from interferences by similarly structured xanthines, such as caffeine and theobromine. Known gas chromatographic methods are more specific, but require derivitization and are time consuming.

Nonisotopic immunoassay techniques are most frequently used because they provide rapid results and are simple to use. Although satisfactory sensitivity has been generally obtained with immunoassay techniques, it has been found recently that they may produce highly elevated results depending upon a patient's renal condition and the specificity of the antibody used in the assay. Moreover, immunoassays require the use of generally costly reagents which have limited staility.

High performance liquid chromatography techniques are also known. These techniques vary in specificity depending upon whether pretreatment of the test sample is carried out. Organic extraction steps are necessary to improve the accuracy and specificity of the assay. Many chromatography methods are susceptible to interferences from a number of substances including some common antibiotics. Other disadvantages include the need for expensive instrumentation and a specialized technical staff to perform the assays.

It is known that theophylline can be determined by measuring its inhibitory effect on alkaline phosphatase activity. However, when assaying human biological fluids in this manner, it is known that endogenous alkaline phosphatase can affect the assay and render inaccurate results on the high side. Endogenous alkaline phosphatase must then be destroyed or removed in some manner prior to the assay to avoid this problem.

In a literature article by B. Vinet and L. Zizian [Clin. Chem., 25:8, pp. 1370-1372 (1979)], an assay for theophylline in human serum is described in which the drug was extracted from the serum sample using chloroform/isopropanol to separate the theophylline from an unknown quantity of endogenous alkaline phosphatase prior to the actual determination of theophylline. The amount of theophylline was determined at pH 9.4 by measuring the amount of inhibition of bovine alkaline phosphatase activity which occurred due to the presence of theophylline. This assay has several serious drawbacks, however. It is limited to solution assays. Further, it is slow and tedious due to the multiple extraction steps required to separate endogenous alkaline phosphatase from theophylline prior to actual determination of the drug.

Therefore, there is a continuing need in the art for a simple and rapid assay for theophylline which assay is unaffected by endogenous alkaline phosphatase, but which also avoids laborious pretreatment or extraction techniques.

SUMMARY OF THE INVENTION

I have found that the present invention overcomes the problems of known theophylline assays. The present invention can be used to determine theophylline by measuring the inhibitory effect on alkaline phosphatase enzyme activity by theophylline. However, unlike the enzyme inhibition assay of Vinet et al, the present invention provides a rapid and simple assay which avoids the effect of endogenous alkaline phosphatase in serum samples without resorting to multistep and laborious procedures taught in the art which include either sample pretreatment or removal of endogenous alkaline phosphatase prior to the assay.

These advantages are achieved by assaying human biological fluids for theophylline at a pH critically lower than the pH taught in the art. It has been found that, at a pH of 9 or less, endogenous alkaline phosphatase is rendered inactive. The assay is then carried out with an isoenzyme of alkaline phosphatase which is active at pH 9 or less. I have further found that this invention can be performed with dry analytical elements containing the isoenzyme and its substrate, which reagents are kept in separate zones of the element until the assay is performed. This invention can readily be adapted for use in highly automated clinical chemistry equipment designed for rapid and simple analytical procedures because pretreatment and extraction steps are unnecessary.

Therefore, in accordance with this invention, a dry analytical element for the determination of theophylline in a human biological fluid comprises an absorbent carrier material, a buffer which maintains the pH at 9 or less during the determination and, in fluid contact, first and second zones. The first zone contains an isoenzyme of alkaline phosphatase which is capable of acting on a substrate for the isoenzyme at a pH of 9 or less. The second zone contains a substrate for the isoenzyme.

An analytical composition for the determination of theophylline in a human biological fluid comprises: an isoenzyme of alkaline phosphatase which is capable of acting on a substrate for the isoenzyme at a pH of 9 or less, a substrate for the isoenzyme, and a buffer which maintains the composition pH at 9 or less.

This invention also provides a diagnostic kit for the determination of theophylline in a human biological fluid. This kit includes: an isoenzyme of alkaline phosphatase which is capable of acting on a substrate for the isoenzyme at a pH of 9 or less, a substrate for the isoenzyme, and a buffer which maintains the pH of the fluid at 9 or less.

Further, a method for the determination oi theophylline in a human biological fluid comprises the steps of:

(A) at a pH of 9 or less, physically contacting a sample of the fluid with both an isoenzyme of alkaline phosphatase which is capable of acting on a substrate for the isoenzyme at a pH of 9 or less, and a substrate for the isoenzyme, to produce a detectable change, and (B) determining the detectable change.

DETAILED DESCRIPTION OF THE INVENTION

The present invention relates to the determination of theophylline in human biological fluids. As used herein, determination refers to qualitative (i.e. mere detection), semi-quantitative or quantitative measurements of the amount of theophylline in a test sample. In particular, this invention can be used to determine theophylline in human biological fluids which contain endogenous alkaline phosphatase (i.e. naturally occurring enzyme) in any of its enzymatic forms (e.g liver, intestinal, placental, bone). For example, this invention can be advantageously used to assay human sera, whole blood, plasma, spinal fluid, sputum, bile, saliva, and the like. It is also possible to use the invention to assay fluid preparations of human tissue such as human skeletal muscle, kidney, placenta, heart, intestine, lung or other tissue. The preferred biological fluids used in the practice of this invention are human sera and whole blood. The assayed fluid need not be diluted, but can be diluted if desired.

Theophylline is determinable in the practice of this invention by inhibiting the activity of alkaline phosphatase, an enzyme which can act on a number of substrates to produce a detectable reaction product. For example, the following representative equation illustrates the production of a detectable dye by the action of alkaline phosphatase using a typical substrate, p-nitrophenyl phosphate:

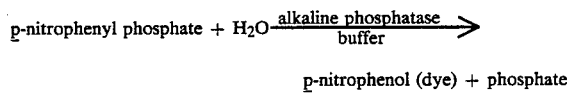

p-nitrophenyl phosphate + H$_2$O $\xrightarrow[\text{buffer}]{\text{alkaline phosphatase}}$ p-nitrophenol (dye) + phosphate The dye can then be colorimetrically detected with suitable spectrophotometric detection equipment. The amount of theophylline present in the test sample contacted with the substrate and enzyme is inversely proportional to the amount of dye measured.

The present invention is practiced at a pH of 9 or less, and preferably at a pH of from 7 to 9. It has been found that endogenous alkaline phosphatase in human fluids does not have significant activity at a pH of 9 or less. Therefore, the presence of human isoenzymes of alkaline phosphatase in a test sample does not adversely affect an assay for theophylline carried out at pH 9 or less. However, isoenzymes of alkaline phosphatase which are not inactivated in an environment of pH 9 or less can be used in the assay to indicate the presence of theophylline. Any isoenzyme from any suitable source which has that desired property, i.e. activity measurable at a pH of 9 or less, is useful in the practice of this invention. Particularly useful isoenzymes are those obtained from bovine sources, e.g. tissues and organs (e.g. liver) of cattle, calves, and the like. Isoenzymes from various other sources (e.g. microorganisms, avian and nonhuman mammalian sources) are also useful. It is well within the skill of a worker in clinical chemistry to find isoenzymes which will be useful in the practice of this invention. This can be done by mixing an isoenzyme and its substrate and observing if any detectable change occurs (e.g. dye is formed) from the enzymatic reaction at a pH of 9 or less.

One or more of a variety of alkaline phosphatase substrates can be used in the practice of this invention. The substrate must be such that upon enzymatic reaction with the isoenzyme, a directly detectable change occurs, e.g. it is converted into one or more detectable reaction products, such as a chromogen, fluorogen, radioisotopically labeled species, and the like. The detectable change measured during the assay can be the appearance or disappearance of such a detectable product, or the change of one detectable product into another. Alternatively, the detectable change can be brought about through a series of reactions which are initiated by the action of the isoenzyme on the substrate. For example, the alkaline phosphatase isoenzyme can act on the substrate to release another enzyme or reagent which then is used in one or more reactions to produce a detectable product. The detectable product may be directly measurable, or require some physical separation or handling for measurement.

In a preferred embodiment of this invention, the assay provides a chromogen or fluorogen as a detectable product of the enzymatic reaction. Generally, the substrates which are useful in such reactions have a phosphate group which is cleaved from the substrate molecule during the enzymatic reaction. Such substrates include organic mono- or diesters of phosphoric acid or salts thereof. Examples of particularly useful substrates include p-nitrophenyl phosphate, phenolphthalein monophosphate, phenolphthalein diphosphate, thymolphthalein monophosphate, indoxyl phosphate, phenyl phosphate, α-naphthol phosphate, β-naphthol phosphate, α-glycerol phosphate, o-methylfluorescein phosphate, o-carboxyphenyl phosphate, alkali metal salts thereof and others known in the art (e.g. U.S. Pat. No. 3,425,912, issued Feb. 4, 1969 to Deutsch et al and European Patent Application No. 61,731, published Oct. 6, 1982). Preferred substrates are p-nitrophenyl phosphate and 4-(4-nitro-2-methylsulfonyl phenylazo)naphthol-1-phosphate.

The theophylline assay can be carried out either in solution or using a dry analytical element. In either procedure, the isoenzyme and substrate must be kept separated until contacted with the liquid test sample.

In solution assay, generally the isoenzyme and substrate are mixed with the liquid test sample in a suitable container (e.g. test tube, petrie dish, beaker, cuvette, etc.). The resulting reaction mixture can be incubated for a period of time at a suitable temperature if desired. The reaction mixture is then evaluated by measuring the resulting detectable change, if any, using conventional detection equipment and procedures. If no change occurs, there is complete inhibition of phosphatase activity by the presence of theophylline in the test sample. If, however, a change occurs, the amount of change observed is then correlated to the amount of theophylline in the liquid sample using conventional procedures. The reaction mixture is buffered to a pH of 9 or less, or preferably from about 7 to about 9. Any suitable buffer or mixture thereof can be used in the practice of this invention as long as it is capable of maintaining the pH during the assay at 9 or less. Representative buffers include, but are not limited to, tris(hydroxymethyl)aminoethane.HCl, glycylglycine, N-tris(hydroxymethyl)-methyl-2-aminoethanesulfonic acid, N-2-hydroxyethylpiperazine-N'-2-ethanesulfonic acid and others known in the art [e.g. Good et al, Biochem, 5(2), 1966, pp. 467–477].

The reagents and materials needed for the practice of this invention can be provided as part of a diagnostic kit for either dry or solution assays. For solution assays, the kit components can be supplied as lyophilized reagents in individual packets having predetermined amounts. Alternatively, they can be provided in bottled or otherwise packaged solutions sufficient in size for one or more assays. Other reagents or non-reactive addenda can also be supplied in the kit along with suitable assay utensils or containers for performing the assay, if desired. A dry analytical element (described below) can also be included as part of a diagnostic kit. In the kit, the substrate and isoenzyme are kept separated until the time of the assay. This can be done with individual packaging or by placing them in separate zones of an element.

Alternatively, the reagents needed for the assay can be obtained from separate sources and brought together to provide an analytical composition.

When the present invention is practiced as a solution assay, the reagent amounts may vary depending upon the substrate used. However, generally, the alkaline phosphatase isoenzyme is present in an amount of from about 50 to about 5,000, and preferably from about 250 to about 2,500, I.U./l. The substrate for the isoenzyme is generally present in an amount of from about 1 to about 100, and preferably from about 10 to about 50, millimolar. The buffer is present in a suitable amount, depending upon the particular buffer, to maintain the pH of the reaction mixture at the desired pH of 9 or less. These buffering amounts can easily be determined by one of ordinary skill in clinical chemistry, but generally are less than about 0.2 molar.

Other optional reagents can also be added to the reaction mixture, if desired. For example, metal ion activators can be added to activate the isoenzymes. Such activators include divalent cations such as $Mg^{++}$, $Co^{++}$, $Mn^{++}$, $Ca^{++}$, $Zn^{++}$, $Sr^{++}$, $Fe^{++}$ and the like, available in free or salt form (e.g. aspartate, acetate, chloride, sulfate, etc.). Alternatively, if the levels of endogenous alkaline phosphatase in the test sample are abnormally high, inhibitors of the enzyme activity may be used. Useful inhibitors include phenylalanine and tetramisole. Such inhibitors advantageously do not affect the activity of some nonhuman alkaline phosphatase isoenzymes.

In addition, one or more phosphate acceptors are preferably included in the reaction mixture to increase the rate of enzyme reaction when phosphate substrates are used. In the art, such a compound is also known as a transphosphorylatable buffer because, in solution assays, it acts as a buffer as well as an acceptor for the phosphate moiety cleaved from the substrate. Useful phosphate acceptors include aminoalcohols or derivatives thereof, or aliphatic amines with the amino alcohols being particularly useful. Examples of such compounds are well known in the art.

The method of this invention can also be practiced with a dry analytical element which comprises an absorbent carrier material, e.g. a thin sheet of a self-supporting absorbent or bibulous material, such as filter paper or strips, which contains the buffer, isoenzyme and substrate described herein. The element is divided into two zones and the isoenzyme and substrate are incorporated into individual zones. Such elements are known in the art as test strips, diagnostic elements, dip sticks, diagnostic agents and the like.

When employed in dry analytical elements, the reagents can be incorporated into a suitable absorbent carrier material by imbibition, impregnation, coating or other suitable technique. Useful absorbent materials are insoluble and maintain their structural integrity when exposed to water or biological fluids such as whole blood or serum. Useful elements can be prepared from paper, porous particulate structures, porous polymeric films, cellulose, wood, glass fiber, woven and nonwoven fabrics (synthetic and nonsynthetic) and the like. Useful materials and procedures for making such elements are well known in the art as exemplified in U.S. Pat. Nos. 3,092,465 (issued June 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al), and 4,270,920 (issued June 2, 1981 to Kondo et al), and 4,312,834 (issued Jan. 26, 1982 to Vogel et al), and U.K. Pat. No. 2,052,057 (published Jan. 21, 1981). The two zones can be separate layers, or finite areas within a single layer. They can be composed of the same or different materials and joined by lamination or other conventional techniques.

Preferably, at least one of the essential zones of the dry analytical elements of this invention is a porous spreading zone which serves as the absorbent carrier material. This zone can be self-supporting (i.e. composed of a material rigid enough to maintain its integrity), but preferably it is carried on a separate supporting substrate (commonly called a support). Such a support can be any suitable dimensionally stable, and preferably, transparent (i.e. radiation transmissive) material which transmits electromagnetic radiation of a wavelength between about 200 and about 900 nm. A support of choice for a particular element should be compatible with the intended mode of detection (reflection or transmission spectroscopy). Useful support materials include paper, metal foils, polystyrene, polyesters [e.g. poly(ethylene terephthalate)], polycarbonates, cellulose esters (e.g. cellulose acetate), etc.

The porous spreading zone can be prepared from any suitable fibrous or non-fibrous material or mixtures of either or both. The void volume and average pore size of this zone can be varied depending upon the use intended. For example, if whole blood or other liquid samples containing high molecular weight materials are to be assayed, the void volume and average pore size are generally greater than if serum or urine is to be assayed.

Useful spreading zones can be prepared using fibrous materials, either mixed with a suitable binder material or woven into a fabric, as described in U.S. Pat. No. 4,292,272 (issued Sept. 29, 1981 to Kitajima et al). Alternatively, and preferably, the spreading zone is prepared from polymeric compositions (e.g. blush polymers) or particulate materials, e.g. beads bound together with or without binding adhesives, as described in U.S. Pat. Nos. 3,992,158 (issued Nov. 16, 1976 to Przybylowicz et al) and 4,258,001 (issued Mar. 24, 1981 to Pierce et al). Other useful spreading zone materials are described in W. German OLS No. 3,150,102 (published July 29, 1982) and Japanese Patent Publication No. 57(1982)-101760 (published June 24, 1982). It is desirable that the spreading zone be isotropically porous, meaning that the porosity is the same in each direction in the zone as caused by interconnected spaces or pores between particles, fibers, polymeric strands, etc.

The elements have two essential zones, at least one of which is preferably a porous spreading zone. The other essential zone can be a reagent zone or a registration zone as those zones are known in the art. The element can have other zones including, but not limited to additional spreading zone, radiation-blocking or filter zones, subbing zones, barrier zones, etc. Preferably, there is a subbing zone between the two essential zones. The subbing zone helps to insure that the isoenzyme and substrate do not interact prior to the assay. The zones are generally in fluid contact with each other, meaning that fluids, reagents and reaction products (e.g. color dyes) can pass or be transported between superposed regions of adjacent zones. Preferably, the zones are separately coated layers, although two or more zones can be a single layer, or a zone can contain two or more separate layers. Besides the references noted above, suitable element components are described, for example, in U.S. Pat. Nos. 4,042,335 (issued Aug. 16, 1977 to Clément), 4,132,528 (issued Jan. 2, 1979 to Eikenberry et al), and 4,144,306 (issued Mar. 13, 1979 to Figueras).

A preferred embodiment of this invention is an element comprising a support having thereon, in order and in fluid contact, a first layer containing the isoenzyme described herein, a radiation-blocking layer, a subbing layer, and a porous spreading layer which contains a substrate for the isoenzyme. The first layer can be a porous spreading layer also, but preferably, it is a reagent or registration layer containing one or more hydrophilic binders (e.g. gelatin, vinyl pyrrolidone polymers, acrylamide polymers, etc.) surfactants, mordants, and other addenda. The subbing layer can comprise one or more subbing materials known to one skilled in the art, e.g. vinyl pyrrolidone polymers, acrylamide polymers, and the like. The radiation-blocking layer generally includes one or more binders, surfactants and reflective materials (e.g. titanium dioxide) which are known in the art.

Optionally, this preferred element can also include a second porous spreading layer which is the outermost layer of the element. The second porous spreading layer can be constructed of materials the same as or different than those in the first porous spreading layer containing the isoenzyme substrate. For example, the first spreading layer can comprise blush polymers prepared according to U.S. Pat. No. 3,992,158, noted above, and the second spreading layer can be composed of particulate materials as described above.

The elements of this invention can also contain one or more other addenda (e.g. surfactants, binders) commonly put in the elements for various manufacturing or operational advantages.

The element contains one or more buffers, as described above, which will maintain the pH of the reaction environment in the element at a pH of 9 or less when the element is used in the assay. It is preferable also that the element contain one or more metal activators and phosphate acceptors as described above.

In an element of this invention, the amount of isoenzyme and substrate can vary widely. Generally, the element contains from about 10 to about 50, and preferably from about 20 to about 40, I.U./m$^2$ of the isoenzyme. The substrate for the enzyme is generally present in an amount of from about 1 to about 5, and preferably from about 2 to about 4, g/m$^2$. The buffer is generally present in a relatively small amount, which amount can be varied depending upon the pH the assay is to be carried out at and the test sample volume. However, for a pH of from about 7 to about 9 and a sample volume of from 1–20 $\mu$l, the amount of buffer is generally from about 0.1 to about 0.7 g/m$^2$. Other addenda are incorporated into the element in amounts which are within the skill of an ordinary worker in clinical chemistry. In the context of this disclosure, I.U. represents the International Unit for isoenzyme activity defined as one I.U. being the amount of isoenzyme activity required to catalyze the conversion of 1 micromole of substrate per minute under standard pH and temperature conditions for the isoenzyme.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, theophylline determination is made by taking the element from a supply roll, chip packet or other source and physically contacting it with a sample (e.g. 1–20 $\mu$l) of the liquid to be tested. Such contact can be accomplished in any suitable manner, e.g. dipping or immersing the element into the sample or, preferably, by spotting the element by hand or machine with a drop of the sample with a suitable dispensing means.

After sample application, the element is exposed to any conditioning, such as incubation, heating or the like, that may be desirable to quicken or otherwise facilitate obtaining any test result.

The alkaline phosphatase present in the element then catalyzes reaction of the substrate at a rate based on the amount of alkaline phosphatase present which is not inhibited by theophylline in the sample. The rate of detectable change (e.g. dye formation) due to formation of the reaction product is quantifiable by passing the element through a zone in which suitable apparatus for reflection or transmission spectrophotometry is provided. Suitable spectrophotometric apparatus and procedures are known in the art. Other suitable detection means include the use of fluorescence spectrophotometry, radiometry, enzyme labeling and the like. The amount of theophylline is inversely proportional to the measured reaction rate.

For example, when p-nitrophenyl phosphate is used as the substrate, the uninhibited enzymatic reaction produces p-nitrophenol which is measurable at 400 nm using a conventional spectrophotometer. The rate of the quantifiable change (e.g. color change) can then be directly related to the rate of substrate reaction which, in turn, is indirectly related to the concentration of theophylline in the sample.

In the following examples, which are provided to illustrate the practice of the invention, the materials used were obtained as follows:

Beef liver alkaline phosphatase isoenzyme, p-nitrophenyl phosphate and tris(hydroxymethyl)aminomethane.HCl buffer from Sigma Chemical Co. (St. Louis, Mo.), polyurethane resin as Estane ™ from B. F. Goodrich (Cleveland, Ohio), Triton ™ X-102, X-200 and X-405 surfactants from Rohm & Haas (Philadelphia, Pa.), and the remaining materials from Eastman Organic Chemicals (Rochester, N.Y.), or prepared using conventional starting materials and procedures.

EXAMPLE 1

Preparation of Theophylline Calibration Curve

A calibration curve for use in the following Examples was prepared in the following manner:

Calibrator samples were prepared by making a stock 4.5 mg/dl theophylline solution by adding 2.25 mg theophylline to 50 ml of pooled human serum. This solution was serially diluted with pooled human serum to give final calibrator solutions having theophylline concentrations of 2.25, 1.125, 0.56 and 0.28 mg/dl of solution.

To 1 cm cells were added 1 ml magnesium acetate ($10^{-3}$ molar final concentration), 500 μl distilled water, 500 μl of each calibrator solution, 100 μl beef liver alkaline phosphatase (1,000 I.U./l final concentration) and 1 ml p-nitrophenyl phosphate (16 mmolar final concentration) in tris(hydroxymethyl)aminoethane.HCl buffer (0.1 molar, pH 8). Control samples contained the buffer alone.

For each calibrator sample, the change in absorbance over time was monitored for several replicates for 5 minutes at 37° C. and 402.5 nm using a conventional Cary 219 Spectrophotometer. The absorbance results were averaged for each sample. The absorbance and % inhibition results are provided in Table I below. A standard calibration curve of percent inhibition vs. theophylline concentration was prepared.

TABLE I

| Theophylline Concentration (mg/dl) | Absorbance (402.5 nm) | % Inhibition |
|---|---|---|
| 0 | 0.143 | 0 |
| 0.28 | 0.135 | 5.6 |
| 0.56 | 0.125 | 12.6 |
| 0.125 | 0.119 | 16.8 |
| 2.25 | 0.100 | 30.1 |
| 4.5 | 0.083 | 42.0 |

EXAMPLE 2

Theophylline Determination in Solution

Ten human serum samples were assayed for theophylline using the procedure described above in Example 1. The predicted theophylline concentrations were obtained from the calibration curve obtained in Example 1. The results are listed in Table II below.

TABLE II

| Test Sample | Absorbance (402.5 nm) | % Inhibition | Predicted Theophylline Concentration (mg/dl) |
|---|---|---|---|
| 0 (Control) | 0.143 | 0 | 0 |
| 1 | 0.116 | 18.9 | 1.3 |
| 2 | 0.145 | 0 | 0 |
| 3 | 0.123 | 14 | 0.82 |
| 4 | 0.142 | 0 | 0.05 |
| 5 | 0.120 | 16.1 | 1.07 |
| 6 | 0.122 | 14.7 | 0.97 |
| 7 | 0.123 | 14.0 | 0.92 |
| 8 | 0.117 | 18.2 | 1.25 |
| 9 | 0.101 | 29.4 | 2.20 |
| 10 | 0.110 | 23.1 | 1.62 |

The ten serum samples were also sent to two independent laboratories to obtain comparative determinations of theophylline.

One laboratory (I) assayed the samples using the commercially available EMIT ™ immunoassay of Syva Corp. (Palo Alto, Calif.).

The second laboratory (II) assayed the samples using the commercially available fluorescence polarization immunoassay of Abbott Laboratories (Chicago, Ill.).

The comparative theophylline concentration data are presented in Table III below.

TABLE III

| Test Sample | Laboratory (I) (mg/dl) | Laboratory (II) (mg/dl) | Present Invention (mg/dl) |
|---|---|---|---|
| 1 | 1.4 | 1.3 | 1.3 |
| 2 | 0.22 | 0.2 | 0 |
| 3 | 0.89 | 0.82 | 0.82 |
| 4 | 2.26 | 2.3 | 0.05* |
| 5 | 1.09 | 1.06 | 1.07 |
| 6 | 0.98 | 0.95 | 0.97 |
| 7 | 0.94 | 0.87 | 0.92 |
| 8 | 1.60 | 1.57 | 1.25 |
| 9 | 2.97 | 2.78 | 2.20 |
| 10 | 1.92 | 1.80 | 1.62 |

The present invention compares well to the standard theophyline assays. The datum point denoted by (*) is believed to be influenced by other health factors peculiar to the patient from which the sample was obtained.

EXAMPLE 3

Theophyline Determination with an Analytical Element

An analytical element having the format and composition illustrated as follows was used to determine theophylline in human serum samples.

| | | Range |
|---|---|---|
| Spreading Layer | Barium Sulfate | 80–150 g/m² |
| | Cellulose acetate | 5–15 g/m² |
| | Polyurethane resin (Estane ™) | 0.5–1.5 g/m² |
| | Triton ™ X-405 surfactant | 0.1–10 g/m² |
| | p-Nitrophenyl phosphate | 1–5 g/m² |
| Subbing Layer | Poly(vinylpyrrolidone) | 1–2 g/m² |
| | Triton ™ X-405 surfactant | 0.05–5 g/m² |
| Radiation-Blocking Layer | Gelatin (hardened) | 1–15 g/m² |
| | Triton ™ X-200 surfactant | 0.01–1 g/m² |
| | Titanium dioxide | 20–50 g/m² |
| Registration Layer | Gelatin (hardened) | 2–20 g/m² |
| | Alkaline phosphatase beef liver isoenzyme | 10–50 I.U./m² |
| | Tris(hydroxymethyl)aminomethane.HCl buffer (pH 8) | 0.1–1 g/m² |
| | Magnesium acetate | 0.005–2 g/m² |
| | Triton ™ X-100 surfactant | 0.1–2 g/m² |
| | Poly(styrene-co-N—vinylbenzyl-N—benzyl-N,N—dimethylammonium chloride-co-divinylbenzene) | 0.5–1.5 g/m² |
| | Poly(ethylene terephthalate) Support | |

The theophylline concentration of each sample was determined by dropping a 10 μl volume of sample onto the porous spreading layer of the element. During incubation at 37° C., the rate of enzyme activity was measured by monitoring the absorbance of resulting dye at 402.5 nm using a conventional clinical chemistry analyzer. The results obtained were compared to results from a commercially available theophylline assay (Abbott). Excellent correlation between the two assays was observed as shown in Table IV below.

TABLE IV

| Predicted Theophyline (μg/ml) | |
|---|---|
| Present Invention | Abbott Reference Immunoassay |
| 5.65 | 4.3 |
| 7.87 | 7.5 |
| 8.25 | 9.6 |
| 11.55 | 11.0 |
| 14.57 | 14.2 |
| 15.82 | 15.8 |

TABLE IV-continued

| Predicted Theophyline (μg/ml) | |
| --- | --- |
| Present Invention | Abbott Reference Immunoassay |
| 16.07 | 17.0 |
| 20.3 | 20.7 |
| 20.5 | 24 |
| 22.9 | 22 |

Correlation statistics: slope of 0.86, intercept of 1.4 and correlation factor (r) of 0.9300.

EXAMPLE 4

Comparative Example

This example illustrates the adverse effect of endogenous alkaline phosphatase on an assay for theophylline when the assay is carried out at a pH greater than 9. An assay of this invention carried out at pH less than 9 is shown for comparison.

Using the assay procedure described in Example 1 above, comparative theophylline assays were carried out at pH 9.5 (prior art method) and pH 8 (method of this invention). Each test solution comprised the following:

500 μl magnesium acetate ($10^{-3}$ molar final concentration),

200 μl beef liver alkaline phosphatase, and 1 ml p-nitrophenyl phosphate (16 millimolar final concentration.

The pH 8 test solution comprised 1 ml tris(hydroxymethyl)aminoethane.HCl buffer (0.15 molar final concentration). The pH 9.5 test solution contained 1 ml adenosine-5'-monophosphate buffer (0.1 molar final concentration).

Serum samples (500 μl) containing either 0 or 20 μg/ml theophylline were added to cuvettes containing either test solution. The serum samples contained either 0 or 1000 I.U./1 of human alkaline phosphatase. The amount of interference by the endogenous (i.e. human) alkaline phosphatase (ALP) is shown in Table V below, represented by the percent change in optical density (O.D.). It can be seen that endogenous alkaline phosphatase exhibits significant interference at pH 9.5, but the interference is minimal with the present invention.

TABLE V

| | O.D./min. at pH 8 | | | O.D./min. at pH 9.5 | | |
| --- | --- | --- | --- | --- | --- | --- |
| Theophylline | ALP (I.U./l) | | % Interference | ALP (I.U./l) | | % Interference |
| Level (μg/ml) | 0 | 1000 | | 0 | 1000 | |
| 0 | 0.62 | 0.66 | 6 | 1.3 | 1.74 | 34 |
| 20 | 0.48 | 0.50 | 4 | 0.76 | 0.98 | 29 |

The invention has been described in detail with particular reference to preferred embodiments thereof, but it will be understood that variations and modifications can be effected within the spirit and scope of the invention.

I claim:

1. A dry analytical element for the determination of theophylline in a human biological fluid, said element comprising an absorbent carrier material, a buffer which maintains the pH at 9 or less during the determination and, in fluid contact, first and second zones, said first zone containing an isoenzyme of alkaline phosphatase which is capable of acting on a substrate for said isoenzyme at a pH of 9 or less, and said second zone containing a substrate for said isoenzyme.

2. The element of claim 1 wherein said substrate is an organic mono- or diester of phosphoric acid.

3. The element of claim 2 wherein said substrate is p-nitrophenyl phosphate or 4-(4-nitro-2-methylsulfonyl phenylazo)naphthol-1-phosphate.

4. The element of claim 1 wherein said isoenzyme of alkaline phosphatase is bovine liver alkaline phosphatase.

5. The element of claim 1 comprising a subbing zone between said first and second zones.

6. A dry analytical element for the determination of theophylline in a human biological fluid, said element comprising a support having thereon, in order and in fluid contact, a first layer containing an isoenzyme of alkaline phosphatase which is capable of acting on a substrate for said isoenzyme at a pH of 9 or less, and a buffer which maintains the pH at 9 or less during the determination, a radiation-blocking layer, a subbing layer, and a porous spreading layer containing a substrate for said isoenzyme.

7. The element of claim 6 wherein said buffer maintains the pH in the range of from about 7 to about 9 during the determination.

8. The element of claim 6 comprising a second porous spreading layer as the outermost element layer.

9. A method for the determination of theophylline in a human biological fluid, said method comprising the steps of:

(A) at a pH of 9 or less, physically contacting a sample of said fluid with both an isoenzyme of alkaline phosphatase which is capable of acting on a substrate for said isoenzyme at a pH of 9 or less, and a substrate for said isoenzyme, to produce a detectable change, and (B) determining said detectable change as an indication of the amount of theophylline in said biological fluid.

10. The method of claim 9 wherein said biological fluid is blood serum or whole blood.

11. The method of claim 9 accomplished with an analytical element comprising an absorbent carrier material, a buffer which maintains the pH at 9 or less during said theophylline determination and, in fluid contact, first and second zones, said first zone containing said alkaline phosphatase isoenzyme, and said second zone containing said substrate for said isoenzyme.

12. The method of claim 9 wherein said isoenzyme of alkaline phosphatase is bovine liver alkaline phosphatase.

13. The method of claim 10 carried out at a pH in the range of from about 7 to about 9.

14. The method of claim 10 wherein said substrate is p-nitrophenyl phosphate or 4-(4nitro-2-methylsulfonyl phenylazo)naphthol-1-phosphate.

15. The method of claim 9 carried out as a solution assay.

* * * * *